United States Patent
Meng et al.

(10) Patent No.: US 11,453,191 B2
(45) Date of Patent: Sep. 27, 2022

(54) MULTILAYER TUBING HAVING LAYERS WITH DIFFERENT PLASTICIZER

(71) Applicant: CAREFUSION 303, INC., San Diego, CA (US)

(72) Inventors: Fanqing Meng, Vernon Hills, IL (US); Marc Weimer, Sandy, UT (US)

(73) Assignee: CAREFUSION 303, INC., San Diego, CA (US)

(*) Notice: Subject to any disclaimer, the term of this patent is extended or adjusted under 35 U.S.C. 154(b) by 305 days.

(21) Appl. No.: 16/656,141

(22) Filed: Oct. 17, 2019

(65) Prior Publication Data
US 2021/0116057 A1 Apr. 22, 2021

(51) Int. Cl.
| | |
|---|---|
| *B32B 1/08* | (2006.01) |
| *F16L 11/10* | (2006.01) |
| *A61L 29/06* | (2006.01) |
| *A61L 29/08* | (2006.01) |
| *A61L 29/12* | (2006.01) |
| *A61L 29/14* | (2006.01) |
| *B32B 7/022* | (2019.01) |
| *B32B 27/08* | (2006.01) |
| *B32B 27/18* | (2006.01) |

(Continued)

(52) U.S. Cl.
CPC .............. *B32B 1/08* (2013.01); *A61L 29/06* (2013.01); *A61L 29/085* (2013.01); *A61L 29/126* (2013.01); *A61L 29/141* (2013.01); *B32B 7/022* (2019.01); *B32B 27/08* (2013.01); *B32B 27/18* (2013.01); *B32B 27/20* (2013.01); *B32B 27/22* (2013.01); *B32B 27/304* (2013.01); *F16L 11/10* (2013.01); *A61L 2420/04* (2013.01); *A61M 5/14* (2013.01); *A61M 25/0045* (2013.01)

(58) Field of Classification Search
CPC .......... B32B 1/08; B32B 7/022; B32B 27/08; B32B 27/18; B32B 27/20; B32B 27/22; B32B 27/30; B32B 27/304; B32B 2250/02; B32B 2250/03; B32B 2250/24; B32B 2307/536; B32B 2535/00; B32B 2597/00; A61L 29/06; A61L 29/085; A61L 29/126; A61L 29/141; A61L 2420/04; A61M 5/14; A61M 25/0045; F16L 11/04; F16L 11/08; F16L 11/10; F16L 11/14
See application file for complete search history.

(56) References Cited

U.S. PATENT DOCUMENTS

| | | |
|---|---|---|
| 4,627,844 A | 12/1986 | Schmitt |
| 4,707,389 A | 11/1987 | Ward |

(Continued)

OTHER PUBLICATIONS

International Search Report and Written Opinion for Application No. PCT/US2020/056127, dated Jan. 25, 2021, 12 pages.

(Continued)

*Primary Examiner* — Walter Aughenbaugh
(74) *Attorney, Agent, or Firm* — Morgan, Lewis & Bockius LLP

(57) ABSTRACT

Tubing, such as medical tubing for administration of intravenous fluid, can include an outer layer on an inner layer, and, optionally additional layers, in which at least the outer layer and the inner layer are made of a same polymeric material but the outer and inner layers have differing amounts or differing types of a plasticizer such that a hardness of the outer layer is greater than a hardness of the inner layer.

20 Claims, 2 Drawing Sheets

(51) Int. Cl.
  *B32B 27/20* (2006.01)
  *B32B 27/22* (2006.01)
  *B32B 27/30* (2006.01)
  *A61M 5/14* (2006.01)
  *A61M 25/00* (2006.01)

(56) References Cited

U.S. PATENT DOCUMENTS

| | | | | |
|---|---|---|---|---|
| 5,241,921 | A * | 9/1993 | Sadlak | B63B 34/60 |
| | | | | 114/253 |
| 5,356,709 | A | 10/1994 | Woo et al. | |
| 6,149,997 | A | 11/2000 | Patel et al. | |
| 6,431,219 | B1 | 8/2002 | Redler et al. | |
| 6,992,138 | B2 * | 1/2006 | Tsuji | C08G 18/0895 |
| | | | | 525/123 |
| 7,815,612 | B2 * | 10/2010 | Cise | A61M 5/142 |
| | | | | 604/246 |
| 2002/0010386 | A1 * | 1/2002 | Matsushita | A61L 29/085 |
| | | | | 600/140 |
| 2008/0188789 | A1 | 8/2008 | Galavotti et al. | |
| 2017/0035018 | A1 * | 2/2017 | Howes | A01J 5/08 |
| 2017/0261132 | A1 | 9/2017 | Garver et al. | |

OTHER PUBLICATIONS

Written Opinion of the International Preliminary Examining Authority for Application No. PCT/US2020/056127, dated Oct. 4, 2021, 5 pages.
International Preliminary Report on Patentability from the International Preliminary Examining Authority for Application No. PCT/US2020/056127, dated Jan. 21, 2022, 17 pages.

* cited by examiner though. Further, plasticized polymeric materials# MULTILAYER TUBING HAVING LAYERS WITH DIFFERENT PLASTICIZER

TECHNICAL FIELD

The present disclosure generally relates to tubing and, in particular, to medical tubing for administration of medical fluid by infusion.

BACKGROUND

Plastic tubing is extensively used in the medical field, particularly for patient analysis and treatment procedures. However, different and sometimes incompatible demands are required for medical tubing. For example, medical tubing should be inert and avoid contamination of fluid transported therethrough. But many plastic materials that have such characteristics tend to be inflexible. In many applications, however, medical tubing is pinched or clamped or used with infusion pumps that move fluid through the tubing by compressing the tubing. Such uses require the tubing to be flexible.

To address the differing demands paced on medical tubing, such tubing has been made with multiple layers of differing polymeric materials or with additives such as plasticizers to change the characteristics of the tubing. However, tubing made of different materials can suffer from delamination and thus sometimes include adhesive "tie layers" between incompatible materials. In addition, tubing made with additives such as plasticizers have the potential of migration and contamination of the additive into fluid transported therethough. Further, plasticized polymeric materials such as plasticized polyvinyl chloride can be sticky and leads to occlusion and tearing of the tubing.

Hence, a continuing need exists for medical tubing that can address differing demands of medical applications.

SUMMARY

Aspects of the subject technology relate to tubing and, in particular, to medical tubing for administration of medical fluid by infusion. In accordance with certain aspects, a tubing can comprise an outer layer on an inner layer, the outer layer and the inner layer can each be made of the same polymeric material, and the outer layer can include a less amount of or a different type of a plasticizer than the inner layer such that a hardness of the outer layer is higher than a hardness of the inner layer. The tubing can include additional layers such as a second inner layer. In certain aspects of the present disclosure, the inner layer can be on the second inner layer and the second inner layer can be made of the same polymeric material as the inner layer. Advantageously, the outer layer can be directly on the inner layer, and the inner layer can be directly on the second inner layer, without an intermediate adhesion layer or tie layer between the outer, inner and/or second inner layers. Such a multi-layered structure can be formed by co-extrusion the outer layer directly on the inner layer, and, optionally, the inner layer directly on the second inner layer, without an intermediate adhesion layer or tie layer between the outer, inner and, optional, second inner layer. Such tubing can be used for administration of intravenous fluid such as by an infusion pump or a part of an infusion set comprising the tubing, which can be bound to a component of such an infusion set such as a medical connector.

Embodiments include one or more of the following features individually or combined. For example, the polymeric material of the layers can be polyvinyl chloride (PVC), and copolymers thereof and blends of such polymers. In some embodiments, the plasticizer is an ester, such as an aliphatic ester or aromatic ester. In other further embodiments, the inner layer has a shore A hardness of 50 to 100. In still further embodiments, the inner layer includes a higher amount of a plasticizer than the outer layer and optional second inner layer such that the hardness of the outer layer and optional second inner layer is at least about 5 hardness units greater than the shore A hardness of the inner layer, e.g., the shore A hardness of the outer layer and optional second inner layer is between and including 5 to about 50 hardness units greater than the hardness of the inner layer.

Additional advantages of the subject technology will become readily apparent to those skilled in this art from the following detailed description, wherein only certain aspects of the subject technology are shown and described, simply by way of illustration. As will be realized, the subject technology is capable of other and different configurations, and its several details are capable of modifications in various other respects, all without departing from the subject technology. Accordingly, the drawings and description are to be regarded as illustrative in nature, and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
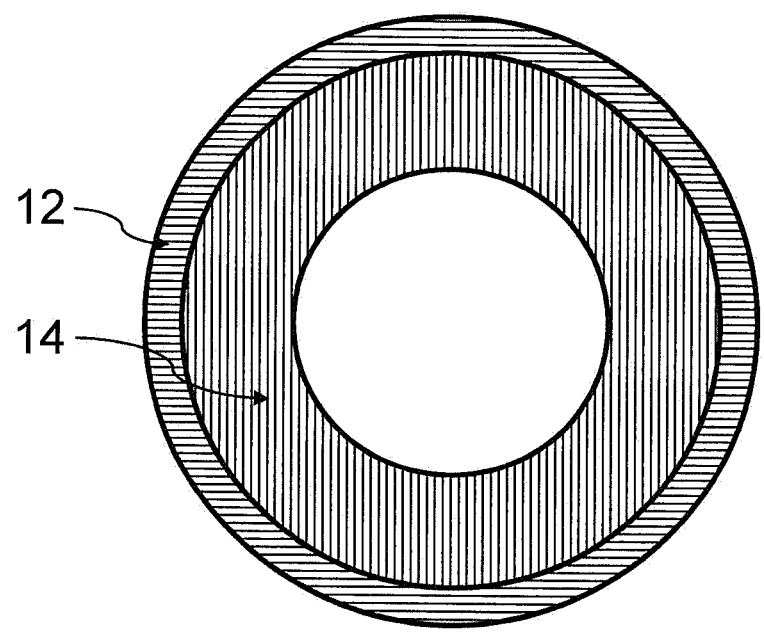
FIG. 1 illustrates a cross-section of a two-layer tubing in accordance with an aspect of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects asnon-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes, examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Aspects of the subject technology relate to tubing and, in particular, to medical tubing for administration of medical fluid by infusion. In accordance with certain aspects, a tubing can comprise a outer layer on an inner layer. Optionally, the tubing can have a second inner layer in which the inner layer is on the second inner layer. Advantageously, the outer layer and the inner layer, and the optional second inner layer, are each made of the same polymeric material but with differing amounts of, or differing types of, a plasticizer, in the various layers such that the hardness of the outer layer is higher than the hardness of the inner layer. In addition, if present, the amount or type of plasticizer in the second inner layer is such that the hardness of the second inner layer is greater than the hardness of the inner layer.

By this construction, tubing of the present disclosure can have the flexibility of a higher plasticized polymeric material, such as the inner layer, while also having a hard, less plasticized outer layer and, optionally, second inner layer. Further, because the layers are made of the same polymeric material, the layers are more readily compatible and can more readily fuse together thereby avoiding or minimizing the need to include an adhesive or tie layer between the outer and inner, and, optionally, third layer greatly simplifying and reducing the cost of the extrusion process for making such tubing.

The hardness of the layers is dependent, in part, on the amount and type of plasticizer in the various layers. Hardness of the layers of the tubing of the present disclosure is determined by a shore A hardness determination such as the method provided by ASTM D2240 that the test measures the penetration of a specified indenter into the material under specified conditions of force and time. In an aspect of the present disclosure, the inner layer includes a higher amount of or a different type of a plasticizer than the outer layer such that the hardness of the outer layer is at least about 5 hardness units greater than the hardness of the inner layer, e.g., greater than about 10, 15, 20, 25, 30, 35, 40, 45, 50, etc. hardness units and values therebetween. Further, if a second inner layer is present in the tubing, the inner layer, e.g., middle layer, includes a higher amount of and/or a different type of a plasticizer than the second inner layer such that the shore A hardness of the second inner layer is greater than the shore A hardness of the inner layer, e.g., the hardness of the second inner layer is at least about 5 hardness units greater than the hardness of the inner layer, e.g., greater than about 10, 15, 20, 25, 30, 35, 40, 45, 50, etc. hardness units and values therebetween. In some embodiments, the inner layer has a shore A hardness of between and including 50 to 100, e.g., less than about 100 such as less than about 90, e.g., less than about 80, 70, 60, 50, etc. The outer and, if present, the second inner layer have a shore A hardness that is at least about 5 hardness units greater than that of the inner layer, e.g., 50, 55, 60, 65, 70, 75, 80, 85, 90, 95, or more.

A plasticizer is an additive that increase the plasticity or decrease the viscosity of a material, e.g., a polymeric material. As used herein a plasticizer is an additive included with a polymeric material which increases the flexibility and reduces the harness of a polymeric material. Plasticizers that can be used with the polymeric materials of the tubing of the present disclosure include, without limitation, an ester including, an aliphatic ester and aromatic ester, a citrate, a dibenzoate, a gluterate, azelate, a terephthalate, a trialkyltrimellitate. Aliphatic esters include, for example, sebacates, adipates such as di(2-ethylhexyl) adipate (DEHA), di(2-ethylhexyl azelate (DOZ), di (2-ethylhexyl sebacate (DOS). citrates such as acetyl tri-n-butyl citrate (ATBC) and n-butyryl-tri-n-hexyl citrate (BTHC), Acetyl tri-n-hexyl Citrae (ATHC) 1,2-cyclohexane dicarboxylic acid diisononyl ester (DINCH), etc. Aromatic esters include, for example, terephthalates, such as di(2-ethylhexyl) terephthalate (DEHT), phthalates, such as di(2-ethylhexyl) phthalate (DEHP), diisononyl phthalate (DINP), bis(2-propylheptyl phthalate (DPHP), diisodecyl phthalate (DIDP), tri-2-ethylhexyl Trimellitate (TOTM). Others include less common polymeric plasticizers and epoxy plasticizers.

Polymeric materials that are useful for layers of the tubing of the present disclosure include, without limitation, medical grade plastic materials such as polyvinyl chloride (PVC), and copolymers thereof and blends of such polymers. Such polymeric materials can be used as the polymeric material for the outer and inner layer of the tubing for the present disclosure. A common medical grade plastic material is PVC. PVC can be made flexible by including varying amounts of plasticizer. For example, phthalate esters such as di(2-ethylhexyl) phthalate (DEHP) and adipate esters such as di(2-ethylhexyl) adipate (DEHA) are commonly used in medical grade polyvinyl chloride tubing.

Tubing of the present disclosure is particularly useful with intravenous assemblies and/or infusion pumps for the transport of intravenous fluid to a patient. An assembly of tubing, valves, fittings, and needles that connect a fluid container to a patient intravenously may be referred to as an "intravenous set" or "IV set". An infusion set can include the tubing according to the present disclosure is bond to components of the IV set such as a medical connector, drip chamber, luer, spike, check valve, filters and needleless valve to name a few to accomplish the medical delivery to patients either to be used as gravity sets or controlled by medical pump for programmed medical delivery procedures Infusion pumps are medical devices that may be used to administer intravenous (IV) fluids. An infusion pump can facilitate the delivery of IV fluids while controlling the volumes and rates for the delivery of such IV fluids. Some infusion pumps move fluid through tubing using a peristaltic pumping mechanism which compresses and releases flexible tubing to force fluid to move through the tube. For use in applications including IV sets and/or infusion pumps, tubing of the present discloser can have an inner diameter for flow of fluid therethrough ranging from about 1.5 mm to about 6 mm, e.g., from 2 mm to 4 mm and an overall sidewall thickness ranging from 0.2 mm to 0.8 mm, such as from 0.4 mm to 0.6 mm. In some aspects of the present disclosure, the outer layer can comprise 10 to 90% of the side wall thickness, the inner layer can comprise 90 to 10% of the sidewall thickness and, if present, the second inner layer can comprise 10 to 90% of the sidewall thickness.

It was found that tubing that with high flexibility and a low hardness could more accurately and precisely deliver a quantity of fluid, and thus more accurately and precisely deliver a quantity of a medicament. However, tubing with low hardness tends to be sticky and tends to tear more readily. On the other hand, tubing with a lower amount of plasticizer tends to be harder but such higher hardness tubing could not maintain pumping delivery accuracy.

For example, a DEHA plasticized PVC material with low Shore A hardness, e.g., Shore A of hardness less than 80, such as 70 or less, can result in very good pumping delivery performance, but the surface is tacky, which is believed due to a high amount of plasticizer on the surface. The surface tackiness of such tubing can cause difficulty IV set assembly process, as well as difficulty in packaging IV sets including such tubing into plastic punch bags. Another potential concern of such tubing is that it more susceptible to damage and tear by the bonding solvents. In contrast, it was observed that a DEHA plasticized PVC material having a Shore A hardness of 80 or higher did not have high surface stickiness on the tubing surface. However, this higher Shore A hardness material could not maintain a pumping delivery accuracy for the particular pump employed due to the high tubing stiffness.

Tubing of the present disclosure can be used to combine the flexibility and low hardness of a highly plasticized polymeric material and with that of a higher hardness lower plasticized polymeric material. Tubing of the present disclosure can be made by a co-extrusion process in which a higher shore A hardness layer is formed as an outer layer while a lower shore A hardness layer is formed as an inner layer. The hardness is adjusted by an amount or type of plasticizer while keeping the chemical composition of polymeric materials for the layers the same. It is understood that the polymeric materials in the different layers can have different molecular weights while still being the same polymeric material having the same chemical composition. In some embodiments, the molecular weight of the polymeric material in the outer and inner and optional second inner layer are substantially the same or the same. In other embodiments, the molecular weights of the polymeric materials in the various layers are different. Such a configuration can reduce or eliminate surface tackiness and improve tubing-female pocket connector bonding strength due to the lower plasticized outer layer while lowering the rigidity of the overall tubing by a low hardness inner layer. In addition, the more stretchable inner layer (higher elongation) will, potentially, be relatively easier to yield to the stress during kinking/bending and prevent from collapsing, thus, to possess an improved kinking resistant.

A further benefit of tubing of the present disclosure is that the outer layer can include one or more of a colorant, UV blocker, radiopaque stripes among other additives. Such additives can be used to design colored tubing and/or light resistant tubing with less concern of such additives leaching to fluid transported by the tubing since the inner layer can prevent migration of such additives. An optional second inner layer with high hardness, less plasticizer or different plasticizer can advantageously reduce an inner layer tackiness during occlusion steps by clamps or by pump's upper stream and downstream valves.

FIG. 1 illustrates a cross-section of a co-extruded double layer tubing configuration in accordance with an aspect of the present disclosure. As shown in the figure, tubing, e.g., medical tubing 10, can include outer layer 12 and inner layer 14. The layers can be co-extruded such that outer layer 12 directly contacts inner layer 14 along the tubing length with no tie layer therebetween. In accordance with the present disclosure, the outer and inner (12, 14) layers are made of the same polymeric material but the hardness of the outer layer (12) is greater than the hardness of the inner layer (14). The differential in hardness can be achieved by including in the polymeric material of the inner layer (14) a higher amount of or a different type of plasticizer than the outer outer layer (12). The amount of or different type of plasticizer should be sufficient to advantageously achieve a hardness of the outer layer to be at least 2 hardness units greater than the hardness of the inner layer. In this example, inner layer 14 has a higher amount of the same plasticizer than outer layer 12 to achieve a lower hardness.

Figure 2:
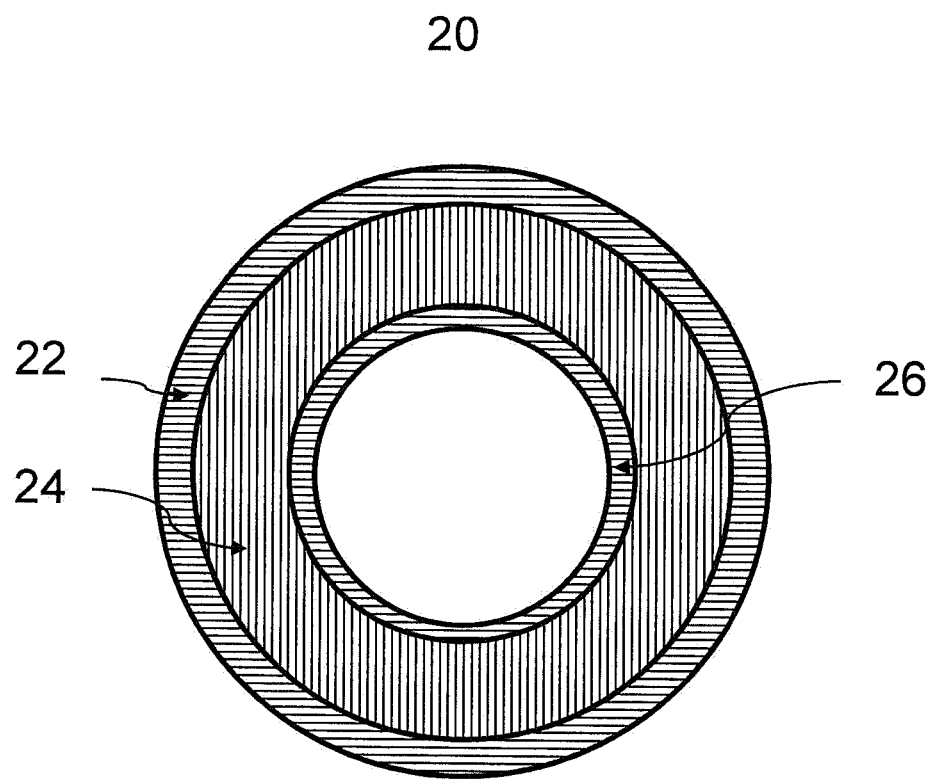
FIG. 2 illustrates a cross-section of a three layer tubing in accordance with an aspect of the present disclosure.

FIG. 2 illustrates a cross-section of a co-extruded three layer tubing configuration in accordance with an aspect of the present disclosure. As shown in the figure, tubing, e.g., medical tubing 20, can include outer layer 22, inner layer 24 and second inner layer 26. The layers can be co-extruded such that outer layer 22 directly contacts inner layer 24, which in turn, directly contacts second inner layer 26 along the tubing length with no tie layer between outer layer and inner layer 24 or between inner layer 24 and second inner layer 26. In accordance with the present disclosure, the outer, inner and second inner layers (22, 24, 26) are made of the same polymeric material but the hardness of outer layer 22 and second inner layer 26 are greater than the hardness of inner layer 24. The differential in hardness can be achieved by including in the polymeric material of inner layer 24 a higher amount of or a different type of plasticizer than outer layer 12 and second inner layer 26. The amount of or different type of plasticizer should be sufficient to advantageously achieve a hardness of the outer or second inner layer to be at least about 5 hardness units greater than the hardness of inner layer 24. In this example, inner layer 24 has a higher amount of the same plasticizer than outer layer 22 and second inner layer 26 to achieve a lower hardness.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than, each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. Medical tubing for administration of medical fluid by infusion, the tubing comprising an outer layer on an inner layer, wherein the outer layer and the inner layer are made of the same polymeric material, and wherein the inner layer includes a higher amount of a plasticizer than the outer layer such that the hardness of the outer layer has a shore A hardness that is a value of at least about 5 greater than a shore A hardness of the inner layer.

2. The tubing of claim 1, wherein the inner layer includes a higher amount of a plasticizer than the outer layer such that the shore A hardness of the outer layer is at least a value of about 10 greater than the shore A hardness of the inner layer.

3. The tubing of claim 1, wherein the inner layer includes a higher amount of a plasticizer than the outer layer such that the shore A hardness of the outer layer is at least a value of about 15 greater than the shore A hardness of the inner layer.

4. The tubing of claim 1, wherein the inner layer has a shore A hardness of between and including 50 to 100.

5. The tubing of claim 1, wherein the outer layer and inner layer are made of polyvinyl chloride as the polymeric material.

6. The tubing of claim 1, wherein the plasticizer is an aliphatic ester or aromatic ester.

7. The tubing of claim 1, wherein the outer layer and the inner layer are co-extruded in direct contact along a length of the tubing.

8. The tubing of claim 1, wherein the outer layer has a thickness that is 10 to 90% of a thickness of the inner layer.

9. The tubing of claim 1, wherein the outer layer includes one or more of a colorant, or UV blocker.

10. The tubing of claim 1, further comprising a second inner layer, wherein the inner layer is on the second inner layer and the second inner layer is made of the same polymeric material as the inner layer.

11. The tubing of claim 10, wherein the inner layer includes a higher amount of a plasticizer than the second inner layer such that the shore A hardness of the second inner layer is at least a value of about 5 greater than the shore A hardness of the inner layer.

12. The tubing of claim 10, wherein the outer layer, the inner layer and the second inner layer are made of polyvinyl chloride as the polymeric material.

13. The tubing of claim 10, wherein the plasticizer is an aliphatic ester or aromatic ester.

14. The tubing of claim 10, wherein the inner layer has a shore A hardness of between and including 50 to 100.

15. The tubing of claim 10, wherein the outer layer, the inner layer and the second inner layer are co-extruded.

16. The tubing of claim 10, wherein the inner layer includes a higher amount of a plasticizer than either the outer layer or the second inner layer such that the shore A hardness of the outer layer and the shore A hardness of the second inner layer are at least a value of about 5 greater than the shore A hardness of the inner layer.

17. A method of forming the tubing of claim 1, the method comprising co-extruding the outer layer directly on the inner layer.

18. The method of claim 17, wherein the outer layer and inner layer are made of polyvinyl chloride as the polymeric material.

19. The method of claim 18, wherein the plasticizer is an aliphatic ester or aromatic ester.

20. An infusion set comprising the tubing of claim 1 bound to a medical connector.

\* \* \* \* \*